(12) United States Patent
Filipon et al.

(10) Patent No.: US 11,369,725 B2
(45) Date of Patent: Jun. 28, 2022

(54) VENTING SYSTEM WITH A VENTING UNIT AND A VENTING DEVICE SET AND METHOD OF OPERATING A VENTING SYSTEM

(71) Applicant: Xenios AG, Heilbronn (DE)

(72) Inventors: Sven Filipon, Heilbronn (DE); Ozan Wagner, Offenau (DE)

(73) Assignee: Xenios AG, Heilbronn (DE)

( * ) Notice: Subject to any disclaimer, the term of this patent is extended or adjusted under 35 U.S.C. 154(b) by 273 days.

(21) Appl. No.: 16/098,162

(22) PCT Filed: Feb. 16, 2017

(86) PCT No.: PCT/DE2017/000030
§ 371 (c)(1),
(2) Date: Nov. 1, 2018

(87) PCT Pub. No.: WO2017/190718
PCT Pub. Date: Nov. 9, 2017

(65) Prior Publication Data
US 2019/0143024 A1  May 16, 2019

(30) Foreign Application Priority Data
May 2, 2016 (DE) ..................... 10 2016 005 338.0

(51) Int. Cl.
*A61M 1/36* (2006.01)
*A61M 1/16* (2006.01)
(Continued)

(52) U.S. Cl.
CPC ............ *A61M 1/3629* (2014.02); *A61M 1/14* (2013.01); *A61M 1/1698* (2013.01);
(Continued)

(58) Field of Classification Search
CPC .. A61M 1/3643; A61M 1/3629; A61M 1/363; A61M 1/3627; A61M 1/14;
(Continued)

(56) References Cited

U.S. PATENT DOCUMENTS 4,850,998 A * 7/1989 Schoendorfer ..... A61M 1/3672
604/28
5,348,533 A * 9/1994 Papillon .............. A61M 1/3644
604/6.07
(Continued)

FOREIGN PATENT DOCUMENTS

EP  0 543 172 A2  5/1993
EP  2 462 967 A1  6/2012
(Continued)

OTHER PUBLICATIONS

International Search Report of PCT/DE2017/000030, dated Jul. 5, 2017.

*Primary Examiner* — Ariana Zimbouski
(74) *Attorney, Agent, or Firm* — Collard & Roe, P.C.

(57) ABSTRACT

A deaerating device set allows a priming circuit to be deaerated fully automatically using a deaerating unit and a priming control unit, a priming liquid container and preferably a priming pump or a priming compressor. A blood pump is operated in a pulsatile manner during the pumping of a priming fluid.

10 Claims, 2 Drawing Sheets

(51) Int. Cl.
*A61M 60/562* (2021.01)
*A61M 1/14* (2006.01)

(52) U.S. Cl.
CPC ........ *A61M 1/3626* (2013.01); *A61M 1/3643* (2013.01); *A61M 1/3644* (2014.02); *A61M 1/3666* (2013.01); *A61M 60/562* (2021.01); *A61M 1/3627* (2013.01); *A61M 2202/0208* (2013.01)

(58) Field of Classification Search
CPC .............. A61M 1/1005; A61M 1/1698; A61M 2202/02; A61M 1/3626
See application file for complete search history.

(56) References Cited

U.S. PATENT DOCUMENTS

| | | | |
|---|---|---|---|
| 9,968,724 B2 | 5/2018 | Utsugida et al. | |
| 2004/0220509 A1* | 11/2004 | Olsen | A61M 1/32 604/6.14 |
| 2014/0174542 A1* | 6/2014 | Jansson | A61M 1/3621 137/1 |
| 2014/0319041 A1* | 10/2014 | Wilt | A61M 1/3609 210/198.1 |

FOREIGN PATENT DOCUMENTS

| | | |
|---|---|---|
| WO | 97/40867 A1 | 11/1997 |
| WO | 2014/162335 A1 | 10/2014 |

\* cited by examiner

VENTING SYSTEM WITH A VENTING UNIT AND A VENTING DEVICE SET AND METHOD OF OPERATING A VENTING SYSTEM

CROSS REFERENCE TO RELATED APPLICATIONS

This application is the National Stage of PCT/DE2017/000030 filed on Feb. 16, 2017, which claims priority under 35 U.S.C. § 119 of German Application No. 10 2016 005 338.0 filed on May 2, 2016, the disclosure of which is incorporated by reference. The international application under PCT article 21(2) was not published in English.

The invention relates to a venting system, a venting unit, a venting device set and a method of operating a venting system. Hereinafter the system is referred to as a venting system. However, the system is also a filling system and the venting unit is also a filling unit and accordingly the venting device set is also a filling device set and the method of operating a venting system is also a method of operating a filling system.

In order to prepare the tube set for cannulation it must be ensured that the tube set is filled with a fluid and contains no air. Before filling with blood, the circulation of a heart-lung machine is filled with a priming fluid. Depending on the clinical picture, before perfusion a mixture of various drugs is added to a circulation which comprises an oxygenator, one or more blood pumps and connection lines. A priming fluid can comprises the following components: 0.9% saline solution, Ringer's lactate solution, HAES, mannitol, heparin, cortisone, sodium bicarbonate solution, tranexamic acid.

For the priming process a priming fluid container with the priming fluid is positioned above the priming circulation so that priming fluid flows into the priming circulation. The priming circulation is then opened at a suitable point so that the air can escape and the entire priming circulation fills with priming fluid. If bubbles are still visible in the priming circulation these are loosened by shaking or knocking in order to ensure that after the priming procedure there is no more air left in the priming circulation.

In doing so it must be ensured that all bubbles have indeed been removed from the priming circulation.

A venting system of the type in question is known from EP 2 462 967 A1. The system described therein was developed for a heart-lung machine. Such devices are used for surgical operations. Their design is very complex and they comprise several pressure sensors, in addition to the priming fluid container in a by-pass at least one reservoir for blood from the blood circulation and an arterial filter for smaller embolisms, particles and bone splinters. As a result the system resistance is greater than in systems for therapeutic procedures which essentially only comprise a blood pump and an oxygenator.

In order to fill a filter with blood from a reservoir particularly slowly, it has been proposed to operate the blood pump at a lower speed at periodic intervals. Though this, the filter is initially only partly filled so that the upper area of the filter membrane remains unwetted by the filling fluid and permeable to air. Air inclusions can thereby transfer from the filtered to the unfiltered side and be removed. The introduced filling fluid passes through the lower part of the filter membrane to the filter outlet side and fills the downstream circulation system. The air cushion that thereby forms in the filter advantageously dampens the flow behaviour of the inflowing filling fluid.

The invention is therefore based on the task of accelerating and simplifying the priming process in therapeutic procedures and at the same time increasing safety as all air bubbles have been removed.

This task is solved with a venting system, a venting unit, a venting device set and a method of operating a venting system disclosed herein. Advantageous further developments are also disclosed.

The venting system according to claim 1 makes an automatic priming process during therapeutic procedures possible. The air sensor is positioned at a point of the priming circulation at which the air bubbles collect in practice. Several air sensors can also be used in order to automatically check different positions for air accumulations.

As the blood pump is a pulsatile pump and is connected to a control unit, the air bubbles in the priming circulation can be removed particularly easily. By way of the control unit the blood pump can thus be operated in a pulsatile manner in order to loosen air bubbles that have become stuck in the tubing or the oxygenator and remove them from the priming circulation. Pulsatile operation results in a jolt at the moment of impulse which changes the position of a stuck air bubble. A pulsatile throughflow thus brings about a brief increase in volume and immediately afterwards a reduction, whereby this process is carried out repeatedly or such fluctuations are used continuously.

In such a system the priming circuit does not usually comprise a reservoir.

A system for therapeutic procedures also does not require a filter in the priming circulation in the direction of flow between the oxygenator and blood pump.

It is particularly advantageous if a priming pump which is connected to the control pump is arranged between the priming fluid container and the priming circulation. In conventional methods the priming fluid is exclusively supplied via the hydrostatic pressure. Through this the container height limits the flow speed of the priming fluid. The use of a priming pump makes it possible to vary the speed of the priming fluid independently of the position of the bag in order to accelerate the priming process. The priming fluid container can therefore also be arranged under the priming circulation if necessary. In this case, during the priming process the primping pump would have to continue operating with a minimum throughflow to ensure that the volume lost through the eliminated air in the system is filled up. A return flow from the priming circulation into the priming fluid container should also be prevented.

Suitable as a priming pump is a roller pump which through its design already prevents an automatic return flow. Advantageous are priming pumps with a throughflow of 0.5 to 10 l/min for example. In order to fill the system as quickly as possible and to allow the air to escape a throughflow of 1 to 4 l/min is preferred.

Also suitable is a pump as is described in EP 2 566 533 A1 and which conveys 9 to 8 l/m at a pressure of max. 550 mmHg for example. However other centrifugal pumps used in medical technology can also be deployed. In centrifugal pumps the priming fluid container should be arranged above the priming circulation unless a zero flow or return flow is prevented by a non-return valve.

In addition and, in particular, alternatively to a priming pump it is proposed that the priming fluid container is connected to a priming compressor in order to build up a pressure in the priming fluid container. Like the priming pump the priming compressor is intended for increasing the volumetric flow of the priming fluid between the priming fluid container and the priming circulation.

To control this volumetric flow the control unit can be connected to the priming compressor in order to regulate the priming compressor.

Alternatively or additionally, between the priming fluid container and the priming circulation a throughflow control unit can be arranged which is connected to the priming control unit. The throughflow control unit can comprise a pump, a valve or a throughflow limiter. This makes it possible to generate with the priming compressor a constant priming fluid pressure above the fluid level in the priming fluid container and by means of the throughflow control unit to control the throughflow between the priming fluid container and the priming circulation. In doing so the throughflow control unit can also be opened in a pulsatile manner in order to produce a pulsing volumetric flow with which the priming fluid can be conveyed to the priming circulation.

An advantageous design of the venting system is achieved by arranging the air sensor in the oxygenator.

As a further development it is suggested that the air sensor or a further air sensor be arranged in one of the connecting lines, preferably at the inlet to the blood pump.

In order to ensure fully automatic running of the priming process, in particular also to operate the pumps in a pulsatile manner, it is proposed that the control unit comprises a memory, in order in particular to store time for operating the blood pump.

If the priming fluid container is connected to the priming fluid container by more than one tube, priming fluid can flow out of the priming fluid container into the priming circulation through one of the tubes while air or priming fluid with air bubbles flows back into the priming fluid container via the other tube.

The task forming the basis of the invention is also solved with a venting unit with a control unit which comprises a data processor that is connected with outlets on the venting unit for connection with at least one air sensor and a blood pump. Such a venting unit serves to control known priming circulations in such a way that fully automatic venting is achieved.

Preferably the data processor of the venting unit is also connected with an outlet on the venting for connection to a blood pump or a compressor.

The venting unit can be designed such that the priming control unit with the data processor and the outlets are arranged in a housing. The venting unit thus forms a compact transportable device which can be connected to a known blood circulation in the priming phase.

For practical application it is particularly advantageous if a venting device set comprises a venting unit and a priming fluid container as elements of a set.

This eventing device set can comprise a priming pump or a priming compressor as a further element.

When carrying out venting it is of particular advantage if the blood pump is operated in a pulsatile manner when pumping the priming fluid.

To ensure reliable venting it is proposed that the control unit controls the venting fully automatically.

Advantageous variants of embodiment are shown in the drawing and are explained below in more detail.

Herein

Figure 1:
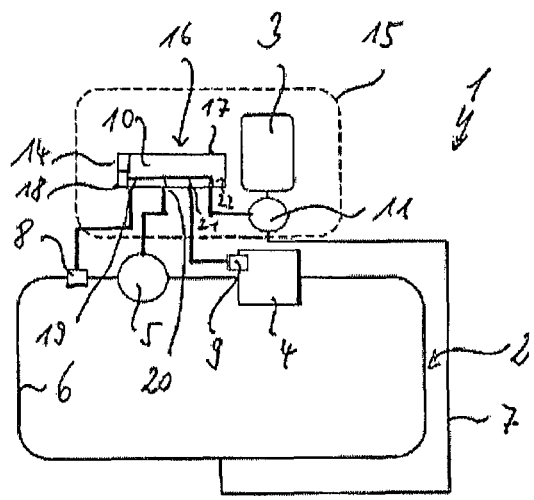
FIG. 1 shows a schematic view of a venting system with a priming pump.

The venting system 1 shown in FIG. 1 comprises a priming circulation 2 and a fluid container 3. The priming circulation 2 essentially consists of an oxygenator 4, a blood pump 5 and connection tubes 6. The priming fluid container 3 is connected to the priming circulation 2 via a tube 7.

The priming circulation 2 has an air sensor 8 before the blood pump 5 in the direction of flow of the blood or the priming fluid, and a further air sensor 9 in an upper area of the oxygenator 4. These air sensors are connected to a priming control unit 10 which in turn is connected to the blood pump 5.

In the first example of embodiment shown in FIG. 1 a priming pump 11 takes over the conveying of priming fluid from the priming fluid container 3 into the priming fluid circulation 2. This priming pump 11 is connected to the priming control unit 10.

Figure 2:
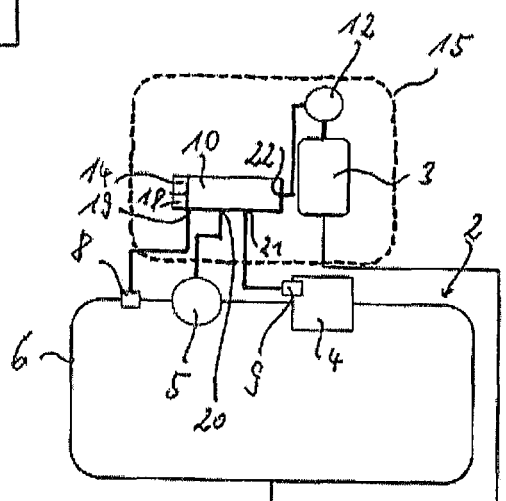
FIG. 2 shows a schematic view of a venting system with a priming compressor.

In the variant of embodiment shows in FIG. 2 the elements of the priming circuit 2 and the priming fluid container 3 are unchanged in comparison with the first variant of embodiment. However, in place of the priming pump 11 a priming compressor 12 is provided which is connected to the priming fluid container 3 and the priming control unit.

Figure 3:
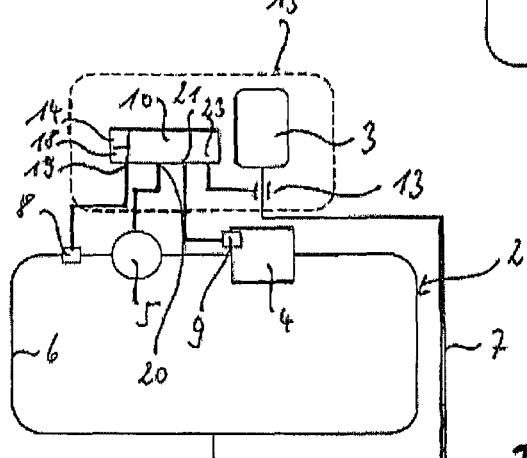
FIG. 3 shows a schematic view of a venting system with an elevated priming fluid container, FIG. 4 schematically shows a venting system with two blood pumps and FIG. 5 schematically shows the course of the process of operating the venting system.

A third variant, without a priming pump 11 and without a priming compressor 12, is shown in FIG. 3. In this example of embodiment the priming fluid container 3 is positioned above the priming circulation 2 so that the priming fluid flows downwards into the priming circulation 2. The other elements of the venting system are designed and arranged as shown in FIGS. 1 and 2.

In all three embodiment variants a throughflow control unit 13, which is connected to the priming control unit 10, can be arranged between the priming fluid container 3 and the priming circulation 2. This throughflow control unit 13 can also only be designed as a measuring device for pressure or volumetric flow in order to measure the throughflow between the priming fluid container 3 and the priming circulation 2 and preferably forward it to the priming control unit 10.

The priming unit 10 comprises a memory 14 in order to store times for operating the blood pump 5 for example.

It is particularly advantageous if the blood pump 5 is designed as a pulsatile blood pump and is controlled by the control unit 10.

The elements of a venting system set are surrounded by dash-dotted line 15. This venting device set essentially comprises a priming fluid container 3 and a venting unit 16. The venting unit 16 has a housing 17 in which the priming control unit 10 with the memory 14 and a data processor 18 is arranged. The data processor 18 is connected with outlets 19, 20, 21 and 22 to the venting unit 16 in order to connect it to the air sensors 8 and 9 and the blood pump 5. The outlet 22 is for the connection with the priming pump 11 or the priming compressor 12. A further outlet 23 can be provided for a connection with the throughflow control unit 13.

Figure 4:
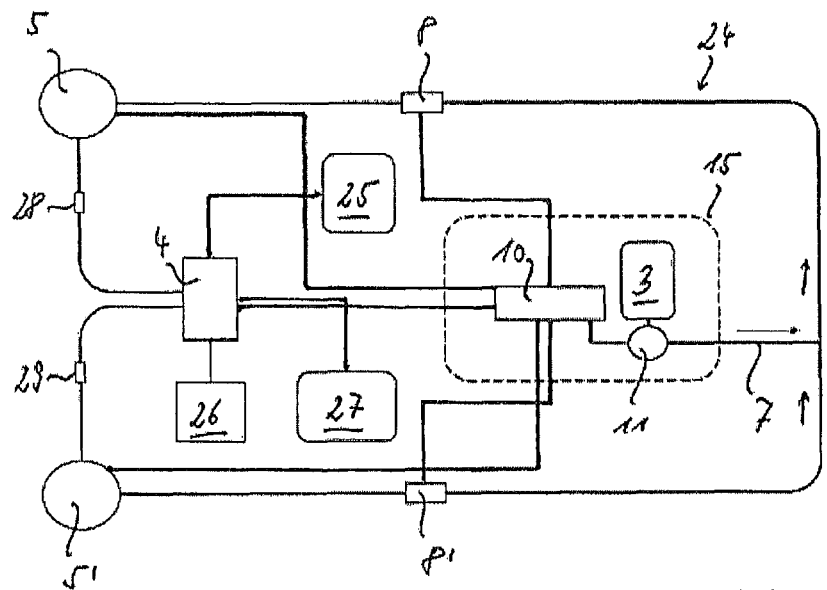

The layout of a venting device set 15 in connection with two blood pumps 5 and 5' is shown in FIG. 4. The venting device set 15 has a connection tube 7 to a priming circulation 24 in which two optical sensors 8 and 8' and two blood pumps 5 and 5' are arranged. An oxygenator 4 in the priming circulation 24 is in connection with a gas supply 25, a blood gas analyser 26 and a heat exchanger 27. Two pressure sensors 28 and 29 monitor the flow of the priming fluid through the blood pumps 5 and 5' before and after the oxygenator 4.

The method of operating a venting system 1 is explained below with the aid of the example of embodiment shown in FIG. 1.

Figure 5:
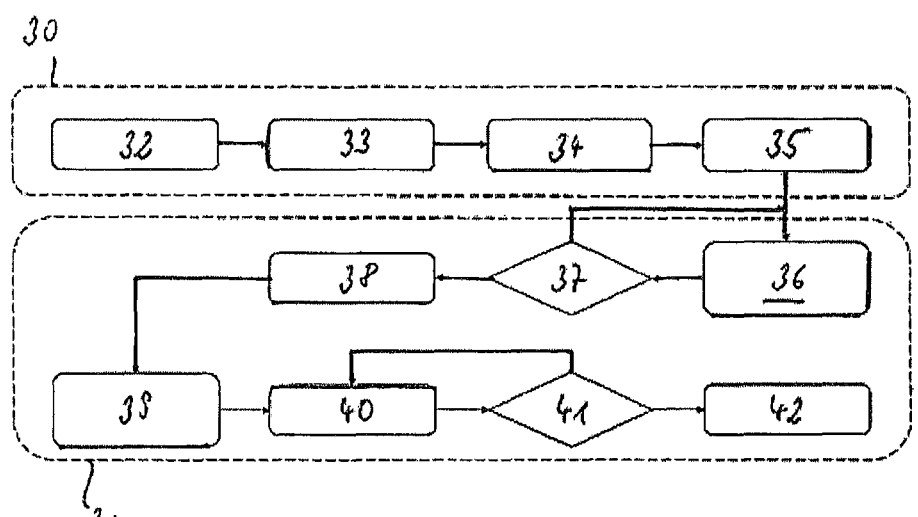

FIG. 5 shows the individual process steps wherein the first four process steps, surrounded with a broken line 30, are carried out manually and the following process steps, surrounded with a broken line 31 can be carried out automatically.

It starts with process stage 32 in which the priming fluid container, in the form of a priming bag for example, is connected to the venting unit 16 via the priming pump 11. In process step 33 the venting unit 16 is then connected to the tubing set, i.e. the venting unit is connected with the air sensors 8 and 9 of the blood pump 5 and the priming pump 11.

In process step 34 the priming unit 10 in the venting unit 16 is then started. As a last manual step 35, which can also be carried out automatically, the priming pump 11 is started (in the example of embodiment shown in FIG. 2 the compressor 12 would be started).

In process step 36 the priming circulation 2 is then filled with priming fluid from the priming fluid container 3 and thereby the oxygenator 4 is vented. In process 37 it is enquired whether the sensor 9 in the oxygenator 4 detects fluid. If it does not detect fluid, by way of process step 36 further priming fluid is pumped into the priming circulation 2.

If the sensor 9 in the oxygenator detects priming fluid in process step 38 the priming pump 11 is stopped and as process step 39 the blood pump 5 in the circulation 2 is started and operated in a pulsatile manner. In process step 40 the blood pump 5 runs in pulsatile mode and conveys residual air into the oxygenator 4 from which the residual air can escape.

In process step 41 the sensor 8 checks whether it detects air bubbles in the priming circulation 2. If air bubbles are detected it continues with process step 40 in which the blood pump 5 conveys the residual air to the oxygenator 4 in pulsatile operation. If in process step 41 the sensor 8 does not detect any air bubbles, in process step 42 the end of venting is initiated in that the blood pump 5 is stopped. The venting device set 15 can then be disconnected from the priming circulation 2.

After connecting the venting device set 15 with the priming circulation 2 the priming circulation 2 can be vented fully automatically and when full venting is shown on the venting unit 16 the venting device set can be removed again from the priming circulation.

As a priming fluid container 3 a priming fluid bag can be used which is renewed when it is empty. However, the container can also be a rigid container with an inlet and an outlet and possibly with an air equalisation line.

The invention claimed is:

1. A venting system with a priming circulation, which comprises an oxygenator, a blood pump and connection tubes and is connected with a priming fluid container, which is connected to the priming circulation,
    wherein the priming circulation has a first air sensor arranged in the oxygenator, a second air sensor arranged in the connection tubes before the blood pump, and a priming control unit,
    wherein the first air sensor and the second air sensor are in connection with the priming control unit and the priming control unit is in connection with the blood pump,
    wherein the blood pump is a pulsatile pump and is in connection with the priming control unit in order, with the priming control unit, to operate the blood pump in such a pulsatile manner that air bubbles that are stuck in the tubing lines or the oxygenator are loosened and removed from the priming circulation, and
    wherein a priming pump, which is in connection with the priming control unit, is arranged between the priming fluid container and the priming circulation.

2. The venting system according to claim 1, wherein the priming circulation does not have a reservoir.

3. The venting system according to claim 1, wherein the priming circulation has no filter in the direction of flow between the oxygenator and the blood pump.

4. The venting system according to claim 1, wherein the priming fluid container is in connection with a priming compressor in order to build up a pressure in the priming fluid container.

5. The venting system according to claim 1, wherein the priming control unit is in connection with a priming compressor in order to regulate the priming compressor.

6. The venting system according to claim 1, wherein between the priming fluid container and the priming circulation a throughflow measuring unit is arranged which is in connection with the priming control unit.

7. The venting system according to claim 1, wherein the priming control unit comprises a memory.

8. The venting system according to claim 1, wherein the priming fluid container is in connection with the priming circulation by way of more than one tubing line.

9. A method of operating the venting system according to claim 1, wherein the blood pump is operated in a pulsatile manner during the pumping of a priming fluid.

10. The method according to claim 9, wherein the priming control unit controls the venting fully automatically.

* * * * *